US012806129B2

(12) United States Patent
Potin

(10) Patent No.: US 12,806,129 B2
(45) Date of Patent: Nov. 24, 2026

(54) COMPOSITION AND METHOD OF USE FOR SCALP AND HAIR CARE AND HAIR GROWTH

(71) Applicant: Frutabomba, Inc., Miami, FL (US)

(72) Inventor: Anthony Potin, Nutley, NJ (US)

(73) Assignee: Frutabomba, Inc., Miami, FL (US)

( * ) Notice: Subject to any disclaimer, the term of this patent is extended or adjusted under 35 U.S.C. 154(b) by 0 days.

(21) Appl. No.: 18/947,043

(22) Filed: Nov. 14, 2024

(65) Prior Publication Data

US 2026/0130835 A1 May 14, 2026

(51) Int. Cl.

*A61K 8/64* (2006.01)
*A61K 8/34* (2006.01)
*A61K 8/9794* (2017.01)
*A61Q 5/12* (2006.01)
*A61Q 19/00* (2006.01)

(52) U.S. Cl.

CPC ................ *A61K 8/64* (2013.01); *A61K 8/345* (2013.01); *A61K 8/9794* (2017.08); *A61Q 5/12* (2013.01); *A61Q 19/007* (2013.01); *A61K 2800/30* (2013.01)

(58) Field of Classification Search

None

See application file for complete search history.

(56) References Cited

U.S. PATENT DOCUMENTS

| | | | |
|---|---|---|---|
| 6,515,007 B2 | 2/2003 | Murad | |
| 8,066,976 B2 | 11/2011 | Preuilh et al. | |
| 9,408,790 B2 | 8/2016 | Bickford | |
| 9,676,696 B2 | 6/2017 | Hakozaki | |
| 11,786,570 B2 | 10/2023 | Herrmann et al. | |
| 2004/0096419 A1 | 5/2004 | Golz-Berner et al. | |
| 2007/0264204 A1 | 11/2007 | Noor et al. | |
| 2011/0232670 A1 | 9/2011 | Molenda | |
| 2014/0161849 A1 | 6/2014 | Bickford | |
| 2020/0155444 A1* | 5/2020 | Farmer | A61K 8/9728 |
| 2020/0206111 A1 | 7/2020 | Lee et al. | |
| 2021/0290707 A1 | 9/2021 | Herrmann et al. | |
| 2023/0338250 A1 | 10/2023 | Lange et al. | |
| 2024/0050348 A1* | 2/2024 | Meyers | A61K 8/42 |

FOREIGN PATENT DOCUMENTS

| | | |
|---|---|---|
| BR | 0611463-6 A2 | 9/2010 |
| EP | 0376821 A1 | 7/1990 |
| ES | 2262957 T3 | 12/2006 |
| JP | 5307366 B2 | 10/2013 |
| KR | 20230167450 A | 12/2023 |
| RU | 2677275 C1 | 1/2019 |
| WO | 2011051948 A2 | 5/2011 |
| WO | 2013110840 A1 | 8/2013 |

OTHER PUBLICATIONS

Quinn "This Shampoo and Conditioner Simultaneously Clarifies and Hydrates Strands—And My 'Combination Hair' Has Never Looked Better" <https://www.wellandgood.com/shopping/coco-and-eve-pro-youth-shampoo-and-conditioner> (Year: 2023).*

Coco & Eve "Pro Youth Hair & Scalp Mask" <https://www.cocoandeve.com/products/pro-youth-hair-scalp-mask> (Year: 2025).*

Ultrus Prospector "RetinoPeptide TM 189" <https://www.ulprospector.com/en/na/PersonalCare/Detail/3030/1474901/RetinoPeptide-189> (Year: 2023).*

Making Cosmetics "Potassium Sorbate" <https://www.makingcosmetics.com/PRV-POSO-02.html?lang=en_US#:~:text=In%20water%20potassium%20sorbate%20releases,as%20preservative%20in%20foods%20&%20cosmetics.&text=Typical%20concentration%200.15%2D0.3%25%20(,in%20combination%20with%20other%20preservatives)> (Year: 2023).*

Symrise "Cosmetic Ingredients Product Catalog" <https://chemspireingredients.com/wp-content/uploads/2016/09/Symrise_Catalog_July_2016.pdf> (Year: 2016).*

Symrise. "RetinoPeptide TM 189: The Peptide Alternative to Retinol" <https://www.ulprospector.com/documents/1601241.pdf?bs=3030&b=1474901&st=1&sl=514856449&crit=a2V5d29yZDpbTXIyaXN0b3lsIE5vbmFwZXBOaWRILTNd&k=Myristoyl|Nonapeptide-3&r=na&ind=personalcare> (Year: 2023).*

Typology. "What is "Sodium Hydroxide" and what is its purpose?" <https://us.typology.com/library/what-is-sodium-hydroxide-and-what-is-its-purpose#chapter-4> (Year: 2023).*

JP5307366B2 Google English Translation; Jan. 18, 2026; pp. 10.

PCT International Search Report; Jan. 20, 2026.

* cited by examiner

*Primary Examiner* — Nicole P Babson

(74) *Attorney, Agent, or Firm* — Geoffrey Lottenberg; Berger Singerman LLP

(57) ABSTRACT

A composition including a retinol-like agent to be used for scalp and hair health and hair growth. In one exemplary embodiment, the composition includes a carrier, a retinol-like agent, and a hydrating agent. Additional ingredients include a solubilizer, a thickener, and a preservation agent to form a scalp serum. In a hair and scalp mask, the composition includes a carrier, one or more conditioning agents, a preservation agent, a moisturizing agent, a retinol-like agent, and at least one pH adjuster. Either the scalp serum or the scalp and hair mask can further include vitamins, proteins, chelating agents, antioxidants, oils, acids, and other actives that promote hair growth.

9 Claims, No Drawings

COMPOSITION AND METHOD OF USE FOR SCALP AND HAIR CARE AND HAIR GROWTH

FIELD OF THE INVENTION

The present invention relates generally to compositions and, more particularly, to a composition including ingredients that are combined with a retinol-like agent to be used for scalp and hair care and hair growth.

DETAILED DESCRIPTION

All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary or the following detailed description. It is also to be understood that the compositions and processes described in the following specification, are simply exemplary embodiments of the inventive concepts defined in the appended claims. Hence, specific compositions relating to the embodiments disclosed herein are not to be considered as limiting, unless the claims expressly state otherwise. The terminology used herein is for the purpose of describing particular embodiments only and is not intended to be limiting of the invention. As used herein, the indefinite articles "a", "an" and "the" should be understood to include plural reference unless the context clearly indicates otherwise. The phrase "and/or," as used herein, should be understood to mean "either or both" of the elements so conjoined, i.e., elements that are conjunctively present in some cases and disjunctively present in other cases.

The term "about" used herein indicates plus or minus+/−5%.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "effective amount" refers to the quantity (or range) of the composition or ingredients thereof necessary to render the desired therapeutic or effective result. For example, an effective amount is a level effective to treat the scalp and promote hair growth. Amounts effective for the particular therapeutic goal sought will depend upon a variety of factors including: the disorder being treated and its severity; the bioavailability, and activity of the specific compound, agent, biologic or pharmaceutical composition used; the route or method of administration and introduction site on the subject; the rate of clearance of the specific compound or biologic and other pharmacokinetic properties; the duration of treatment; inoculation regimen; ingredients used in combination or coincident with the specific compound, biologic or composition; the age, body weight, sex, diet, physiology and general health of the subject being treated; and like factors well known to one of skill in the relevant scientific art. Some variation in dosage or amounts will necessarily occur depending upon the condition of the subject being treated.

As used herein, the term "administering" refers to providing an effective amount of the present composition to a person via any of a number of potential delivery mechanisms, including, without limitation, transdermal, topical, transfollicular, and/or the like. The composition of the present invention can be administered individually but may also be administered with other compounds, excipients, fillers, binders, carriers, or other vehicles selected based on the chosen route of administration and standard pharmaceutical practice. Administration may be by way of carriers or vehicles, such as injectable solutions, including sterile and non-sterile aqueous or non-aqueous solutions, or saline solutions; creams; lotions; serums; oils; multi-phase systems; capsules; tablets; granules; pellets; powders; suspensions, emulsions, or microemulsions; patches; micelles; liposomes; vesicles; implants, including micro-implants; eye drops; synthetic polymers; microspheres; nanoparticles; and the like.

As used herein, "retinol-like agent" refers to an active ingredient with a biological activity profile the same as or substantially similar to retinol, but without a retinoid structure. Such retinol-like agents include synthetic lipo-peptides such as, and without limitation, myristoyl nonapeptide-3, which is the active ingredient in the composition known as Retinopeptide 189. Retinopeptide 189 is a composition of myristoyl nonapeptide-3, pentylene glycol, glycerin, and water. The retinol-like agent may be formulated in any galenic form and devoid of any retinoids. The retinol-like agent may also include, without limitation, Bakuchiol, Picao Preto extracts (e.g., Revinage WPO), Mangixyl, and milk thistle extract (e.g., Siliphos). Galenic forms include aqueous or oily lotions, oil-in-water or water-in-oil emulsions, multi-phase galenic forms (e.g., bi-phase, tri-phase), and liquid, solid, or powder forms.

In one of its broad aspects, this invention embodies a process that comprises combining a retinol-like agent with other active ingredients to provide a composition intended to be administered onto a scalp to promote scalp and hair health and/or hair growth. In its broadest form, the composition includes a retinol-like agent, such as Retinopeptide 189, of about 1% by weight, which is combined with other active ingredients to produce a compound targeting scalp and hair health and promoting hair growth. In this embodiment, the composition is devoid of retinol or retinoids.

In a first aspect, the invention relates to a scalp serum composition comprising at least one carrier, at least one retinol-like agent, at least one hydrating agent, and, optionally, at least one preservation agent. In an alternative embodiment, the scalp serum composition may comprise at least one carrier, at least one retinol-like agent, at least one thickener, at least one hydrating agent, and, optionally, at least one preservation agent. In some embodiments, if the composition is anhydrous, no preservation agent may be necessary.

In another exemplary embodiment, the scalp serum includes at least one solubilizer. The solubilizer in one exemplary embodiment may comprise an organic solvent, which can denote a compound that is liquid at room temperature and water-miscible in water of greater than 50% by weight at 25° C. and atmospheric pressure. One example of a solubilizer is glycol (which may also function as a hydrating agent as described below). Examples of water-soluble solvents include, without limitation, monoalcohols and monomeric polyols. Non-limiting examples of lower monoalcohols are those containing from 1 to 8 carbon atoms, such as ethanol and isopropanol, glycols containing from 2 to 8 carbon atoms, such as, ethylene glycol, propylene glycol, 1,3-butylene glycol and dipropylene glycol, caprylyl glycol, C3 and C4 ketones and C2-C4 aldehydes. Examples of water-soluble organic solvents include but are not limited linear or branched C2-C4 alkanols, such as ethanol and isopropanol; polyols and polyol ethers, for instance 2-butoxyethanol, glycerol/glycerin, propylene glycol, dipropylene glycol, polyethylene glycols, propylene glycol monomethyl ether, diethylene glycol monomethyl ether and monoethyl ether, and also aromatic alcohols, for instance benzyl alcohol or phenoxyethanol, and mixtures thereof. Alternatively, in another exemplary embodiment of water-soluble solvents, the composition may include without limitation one or more monomeric polyols. These include without limitation monomeric polyols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol. Non-limiting examples of monomeric polyols having one or more aliphatic diols include 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and mixtures thereof.

In one non-limiting embodiment, the carrier includes a soluble liquid, such as water, at a quantity sufficient for the composition to reach 100%. The retinol-like agent may comprise Retinopeptide 189 in an effective amount of about 1% by weight. The percentage of retinol-like agent may vary depending on the purpose of the composition's application. For example, the composition can include a retinol-like agent within a range of up to about 10% or more.

As iterated above, in some embodiments, the composition includes ingredients known to preserve or stabilize the formula, such as preservatives, co-preservatives, anti-oxidants, and chelating agents. In some embodiments, the composition includes one or more preservatives, co-preservatives or anti-bacterial ingredients that include without limitation glycerin derivative compounds (e.g., glycerin, ethylglycerin, ethylhexylglycerin), phenoxyethanol, pentylene glycol, 1,2 hexanediol, caprylyl glycol, benzyl alcohol, parabens (methylparaben, ethylparaben, propylparaben, butylparaben, isobutylparaben, etc.), benzoic acid and its salts, sorbic acid and its salts, salicylic acid and its salts, zinc pyrithione, dehydroacetic acid and its salts, chlorphenesin, triclosan, formaldehyde, DMDM hydantoin, imidazolidinyl urea, diazolidinyl urea, quaternium-15, methylisothiazolinone, methylchloroisothiazolinone, 2-bromo-2-nitropropane, chlorhexidine digluconate, polyaminopropyl biguanide, benzalkonium chloride, neem Oil, essential Oils (various) or combinations thereof.

The composition can also comprise anti-oxidants, including without limitation vitamin E, pentaerythrityl tetra-di-t-butyl hydroxyhydrocinnamate, octadecyl di-t-butyl-4-hydroxyhydrocinnamate, vitamin C and its derivatives, polyphenols, or combinations thereof.

The composition can also comprise chelating agents such as ethylenediamine-tetraacetic acid (EDTA) and its salts, sodium phytate, phytic acid, sodium gluconate, trisodium ethylenediamine disuccinate, s,s-ethylenediamine-n,n'-disuccinic acid, tetrasodium glutamate diacetate, sodium citrate or combinations thereof.

The total amount of the one or more preservatives, co-preservatives, anti-oxidant or chelating agent if added to the composition, may vary. In some cases, the amount of the one or more preservatives, co-preservatives, anti-oxidant or chelating agent is about 0.01 to about 10 wt. %, about 0.1 to about 6 wt. %, about 0.15 to about 3 wt. %, or about 1 to about 3 wt. %, based on the total weight of the composition.

A thickener and/or a stabilizer up to about 5% by weight may be added to the composition. Non-limiting examples include acacia gum, agar, algin, alginic acid, ammonium alginate, amylopectin, calcium alginate, sodium alginate, calcium carrageenan, carnitine, carrageenan, dextrin, gelatin, gellan gum, guar gum, tragacanth gum, acacia gum, arabic gum, guar hydroxypropyltrimonium chloride, hydroxypropyl guar hydroxypropyltrimonium chloride, hectorite, hyaluronic acid, hydrated silica, hydroxypropyl guar, karaya gum, kelp, locust bean gum, natto gum, potassium alginate, potassium carrageenan, propylene glycol alginate, sodium carboxymethyl dextran, sodium carrageenan, tragacanth gum, xanthan gum, modified xanthan gum, biosacharide gum, chitin, levan, elsinan, collagen, gelatin, zein, gluten, soy protein, casein, and mixtures thereof. Additional non-limiting examples of thickeners include without limitation pullulan, hydroxypropylmethyl cellulose, hydroxyethyl cellulose, hydroxypropyl cellulose, hydroxymethyl cellulose, polyvinyl pyrrolidone, carboxymethyl cellulose, carboxyvinyl polymer, dextrin, polyvinyl alcohol, carboxylated polyvinylalcohol, sulfonated polyvinyl alcohol, starch, starch derivatives, hemicellulose, hemicellulose derivatives, proteins, chitosan, hydroxypropyl chitosan, chitosan derivatives, polyethylene glycol, tetramethylene ether glycol, and mixtures thereof.

The composition may include acrylate copolymers: carbomer, acrylates copolymer, acrylates/C10-30 alkyl acrylate crosspolymer, acrylates/octylacrylamide copolymer, acrylates/t-butylacrylamide copolymer, ammonium acryloyldimethyltaurate/carboxyethyl acrylate crosspolymer, hydroxyethyl acrylate/sodium acryloyldimethyl taurate copolymer, sodium acrylate/acryloyldimethyltaurate/dimethylacrylamide crosspolymer, acrylates/acrylamide copolymer, glyceryl acrylate/acrylic acid copolymer, acrylates/beheneth-25 methacrylate copolymer, acrylates/C12-22 alkyl methacrylate copolymer, polyacrylate crosspolymer-11. Other polymers include sodium polyacryloyldimethyl taurate, sodium acryloyldimethyltaurate/VP crosspolymer, ammonium acryloyldimethyltaurate/beheneth-25 methacrylate crosspolymer, hydroxyethyl acrylate/sodium acryloyldimethyl taurate copolymer.

The hydrating agent, if any, included in the composition includes without limitation humectants and emollients up to an amount of about 40% by weight. In alternative exemplary embodiment, the composition includes without limitation humectants and emollients in a range of about 5% or about 40% by weight. Such hydrating agents including, without limitation, aloe vera gel (or equivalent by weight of powder or extract, when reconstituted), hyaluronic acid, vitamin B5, ceramides, and glycols.

In some embodiments, the compositions for the scalp serum can include additional active ingredients, such as, without limitation, ingredients for soothing, moisture, and nourishment. The compositions can include vitamins (not limiting examples: biotin, panthenol, niacinamide, tocopherol, Vitamin C) or their derivatives, analogs, or associations. The compositions can also include amino-acids, peptides, or proteins. Examples of peptides include acetyl tetrapeptide-3 (derived from a signal peptide which stimulates tissue remodeling), oligopeptide-2 (plant growth factor), biotenyl tri-peptide-1 (promoting hair bulb proliferation), copper tripeptide-1, myristoyl hexapeptide-16, sh-oligopeptide-78, oligopeptide-54, acetyl tetrapeptide-3, acetyl hexapeptide-1, palmitoyl tetrapeptide-20 amide, *Avena sativa* (Oat) peptide. Other active ingredients may include anti-aging ingredients or other hair growth ingredients. Such other hair growth ingredients include, without limitation, minoxidil, finasteride, Skinhairgium bio (maca extract+maltodextrin), and Redensyl (glycerin+aqua+sodium metabisulfite+*Larix europaea* wood+glycine+zinc chloride+*Camellia sinensis* leaf extract), Capixyl (butylene glycol (and) aqua (and) dextran (and) acetyl tetrapeptide-3 (and) *Trifolium pratense* (clover) flower extract). Further still, other active ingredients may be included, such as pre- or post-biotics, caffeine, and the like up to an amount of about 10% by weight. The composition in one exemplary embodiment is formulated into a serum that is administered onto the scalp of a person. An embodiment of the composition of the scalp serum comprises:

TABLE 1

Composition for Scalp Serum

| Ingredients | Percentage by Weight |
|---|---|
| Water | QSP 100 |
| Retinol-like agent (Retinopeptide 189) | 0.1-10 |
| Glycols | 0.5-15 |
| Xanthan gum | 0.05-2 |
| Preservation Agent | 0.2-10 |
| Aloe Vera | 5-40 |
| Other Active agents | 0.1-10 |

In a second aspect, the invention relates to a scalp and hair mask composition comprising at least one carrier, one or more conditioning agents, at least one preservation agent, at least one moisturizing agent, at least one retinol-like agent, and, optionally, at least one pH adjuster.

The conditioning agent in one exemplary embodiment includes, without limitation, quaternary ammonium salts, cationic polymers, non-silicone fatty compounds, silicones, cationic proteins, cationic protein hydrolysates, oils, ester oils, alkyl amines, and combinations thereof. In some embodiments, the composition includes silicones including, without limitation, polyorganosiloxanes, polyalkylsiloxanes, polyarylsiloxanes, polyalkarylsiloxanes, polyestersiloxanes, and combinations thereof; dimethicone, cyclomethicone (cyclopentasiloxane, cyclohexasiloxane), amodimethicone, trimethyl silyl amodimethicone, phenyl trimethicone, trimethyl siloxy silicate, polymethylsilsesquioxane and combinations thereof. Other conditioning agents include vegetable oils, quaternium ammonium salts such as without limitation behentrimonium chloride, cetrimonium chloride, or quaternium-free agents such as without limitation brassicy valinate esylate; fatty alcohols and esters. The conditioning agent, if any, in the composition may comprise an effective amount in the range of up to 20% by weight.

The pH adjusters include without limitation citric acid, lactic acid, sodium hydroxide, or arginine in an amount up to 3% by weight.

Preservation agents may include any one or any combination of the preservatives, co-preservatives, anti-oxidants, and chelating agents listed hereinabove in an amount of up to 5%. For example, the one or more preservatives, co-preservatives or anti-bacterial ingredients include but not limited to glycerin containing compounds (e.g., glycerin, ethylglycerin, ethylhexylglycerin), phenoxyethanol, benzyl alcohol, parabens (methylparaben, ethylparaben, propylparaben, butylparaben, isobutylparaben, etc.), benzoic acid and its salts, sorbic acid and its salts, salicylic acid and its salts, zinc pyrithione, dehydroacetic acid and its salts, chlorphenesin, triclosan, formaldehyde, DMDM hydantoin, imidazolidinyl urea, diazolidinyl urea, quaternium-15, methylisothiazolinone, methylchloroisothiazolinone, 2-bromo-2-nitropropane, chlorhexidine digluconate, polyaminopropyl biguanide, benzalkonium chloride, neem Oil, essential Oils (various) or combinations thereof.

Anti-oxidants, including without limitation vitamin E, pentaerythrityl tetra-di-t-butyl hydroxyhydrocinnamate, octadecyl di-t-butyl-4-hydroxyhydrocinnamate, vitamin C, E and its derivatives, polyphenols, or combinations thereof.

The chelating agents include but are not limited to ethylenediamine-tetraacetic acid (EDTA) and its salts, sodium phytate, phytic acid, sodium gluconate, trisodium ethylenediamine disuccinate, S,S-ethylenediamine-N,N'-disuccinic acid, Tetrasodium Glutamate Diacetate, sodium citrate or combinations thereof.

In some embodiments, the compositions for the scalp and hair mask composition can include additional active ingredients, such as without limitation ingredients for soothing, moisture, nourishment, including vitamins or certain peptides like acetyl tetrapeptide-3 (derived from a signal peptide which stimulates tissue remodeling), oligopeptide-2 (plant growth factor) or biotenyl tri-peptide-1 (promoting hair bulb proliferation). Other active ingredients may include secondary or supplemental active ingredients for stimulating hair growth or to promote anti-aging. Such other active ingredients may include peptides. Examples of peptides include acetyl tetrapeptide-3 (derived from a signal peptide which stimulates tissue remodeling), oligopeptide-2 (plant growth factor), biotenyl tri-peptide-1 (promoting hair bulb proliferation), copper tripeptide-1, myristoyl hexapeptide-16, sh-oligopeptide-78, oligopeptide-54, acetyl tetrapeptide-3, acetyl hexapeptide-1, palmitoyl tetrapeptide-20 amide, *Avena sativa* (Oat) peptide. Further still, other active ingredients may be included, such as pre- or post-biotics, caffeine, and the like up to an effective amount of about 10% by weight. In some exemplary embodiments and without limitation, the scalp and hair mask composition can include active ingredients for growth, such as those listed herein above in the serum composition.

A fragrance agent that is natural, synthetic or a mixture of both may be added to the scalp and hair mask composition up to an amount of about 2% or less by weight.

Non-limiting embodiments of the composition of the hair and scalp mask are as follows.

TABLE 2

Composition for Hair and Scalp Mask

| Ingredients | Percentage by Weight |
|---|---|
| Water | QSP 100 |
| Retinol-like agent (Retinopeptide 189) | 0.01-10% |
| Silicone | 0.1-10 |
| Emollients | 0.1-10 |
| Vegetable oils | 0.1-10 |
| Quaternary ammonium salt | 0.5-7 |
| Fatty alcohol and/or esters | 0.5-20 |

TABLE 2-continued

| Composition for Hair and Scalp Mask | |
|---|---|
| Ingredients | Percentage by Weight |
| Glycols | 0.5-5 |
| Preservation Agent | 0.2-5 |
| Fragrance | 0.5-1.5 |
| pH Adjusters | 0.001-3 |

TABLE 3

| Composition for Hair and Scalp Mask | |
|---|---|
| Ingredients | Percentage by Weight |
| Water | QSP 100 |
| Retinol-like agent (Retinopeptide 189) | 0.01-10% |
| Emollients | 0.1-10 |
| Vegetable oils | 0.1-10 |
| Quaternary ammonium salt | 0.5-7 |
| Fatty alcohol and/or esters | 0.5-20 |
| Glycols | 0.5-5 |
| Preservation Agent | 0.2-5 |
| Fragrance | 0.5-1.5 |
| pH Adjusters | 0.001-2 |

TABLE 4

| Composition for Hair and Scalp Mask | |
|---|---|
| Ingredients | Percentage by Weight |
| Water | QSP 100 |
| Retinol-like agent (Retinopeptide 189) | 0.01-10% |
| Silicone | 0.-1-10 |
| Emollients | 0.-1-10 |
| Vegetable oils | 0.1-10 |
| Quaternium-free conditioning agents | 0.5-7 |
| Fatty alcohol and/or esters | 0.5-20 |
| Glycols | 0.5-5 |
| Preservation Agent | 0.2-5 |
| Fragrance | 0.5-1.5 |
| pH Adjusters | 0.001-2 |

In an alternative embodiment, the hair and scalp mask composition includes additional ingredients that further activate hair growth stimulation (for example and without limitation any of the growth activation ingredients disclosed herein above in the serum composition), improve scalp health, or reinforce the hair fiber at the cortex or the cuticle levels. These additional ingredients include, for example, a mixture of hydroxypropylgluconamide and hydroxypropylammonium; hydrogenated castor oil/sebacic acid copolymer; proteins and derivatives; peptides and derivatives; amino-acids and derivatives; and/or mixtures of hydrolyzed vegetable proteins, amino-acids and mixtures. The composition may also include vitamins, including without limitation B5, E, B3, C, Biotin and derivatives.

An embodiment of this composition of the hair and scalp mask is as follows:

TABLE 5

| Composition for Hair and Scalp Mask | |
|---|---|
| Ingredients | Percentage by Weight |
| Water | QSP 100 |
| Retinol-like agent (Retinopeptide 189) | 0.01-10% |
| Silicone | 0.1-10 |
| Vegetable oils | 0.1-10 |
| Quaternary ammonium salt | 0.5-7 |
| Fatty alcohol and esters | 0.5-20 |
| Glycols | 0.5-5 |
| Preservation Agent | 0.2-5 |
| Fragrance | 0.5-1.5 |
| Citric acid or Lactic acid | 0.001-1 |
| Sodium Hydroxide or Arginine | 0.001-1 |
| Hydroxypropylgluconamide + Hydroxypropylammonium Gluconate | [0.1-5%] |
| Hydrogenated Castor Oil/Sebacic Acid Copolymer | [0.05-5%] |
| Proteins | [0.01-5%] |
| Vitamins | [0-5%] |
| Sodium phytate | [0.01-1%] |
| Anti-oxidants | [0.01-2%] |

The compositions disclosed herein promote hair health and growth, creating fuller, denser and thicker hair, via the use of a retinol-like agent while being free of retinol/retinoid which may otherwise have an irritating effect on the skin, scalp, or hair follicle. In some embodiments the retinol-like agent can be a peptide which can potentially have further repairing effects on the fiber directly due to its size and ability to penetrate and repair hair cortex itself beyond the positive effects of using retinol-like agent.

In one non-limiting embodiment, a method for using the scalp serum composition is described. The method includes providing a scalp serum comprising a combination of the ingredients described in greater detail above and using a delivery system, such as an aqueous solution to administer an effective amount of serum onto the person's scalp. In one exemplary embodiment, the effective amount of serum administered to a person's scalp is about 0.5 to 5 ml per day and is left there for the scalp to absorb. Topical application of scalp serum results in the scalp absorbing the composition and reaching the follicles on the scalp.

In another non-limiting embodiment, a method for using a scalp and hair mask composition is described. The method includes providing a scalp and hair mask comprising a combination of the ingredients described in greater detail above and using a delivery system, such as an oil-in-water emulsion, that is spread on the scalp and hair. The emulsion is then left on the scalp and hair for about 3 to 30 minutes to administer an effective amount of composition mask onto the person's scalp and hair to promote scalp and hair health and hair growth. During the applicable period, the actives can be delivered to both the scalp skin as well as the hair fiber or follicle before it is rinsed out.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A composition for a hair and scalp mask, comprising, at least one carrier, one or more conditioning agent, one or more preservatives, one or more moisturizing agent, and at least one retinol-like agent comprising a mixture of at least myristoyl nonapeptide-3, pentylene glycol, glycerin, and water in an effective amount in the range of 0.01% to less than and not equal to 1% by weight.

2. The composition of claim 1, further comprising a fragrance agent.

3. The composition of claim 1, wherein the composition does not contain retinol or retinoid.

4. The composition of claim 1, wherein one of the at least one carrier comprises a soluble liquid.

5. The composition of claim 1, wherein at least one of the one or more conditioning agent comprises silicone, vegetable oil, fatty alcohol, ester, quaternary ammonium salt or quaternium-free conditioning agent.

6. A composition for a hair and scalp mask, comprising:

a soluble liquid;

a first conditioning ingredient in an effective amount in the range of about 0.001% to about 10% by weight;

a second conditioning ingredient comprising quaternary ammonium salt or quaternium-free conditioning agent including at least one of behentrimonium chloride, cetrimonium chloride, or brassicyl valinate esylate in an effective amount in the range of about 0.5% to about 7% by weight;

a third conditioning ingredient comprising a fatty alcohol or ester in an effective amount in the range of about 0.5% to about 20% by weight;

a retinol-like agent comprising a mixture of at least myristoyl nonapeptide-3, pentylene glycol, glycerin, and water in an effective amount in the range of 0.01% to less than and not equal to 1% by weight;

a moisturizing ingredient comprising at least one glycol in an effective amount in the range of about 0.001% to about 5% by weight;

a preservative in an effective amount in the range of about 0.2% to about 5% by weight;

a fragrance agent in an effective amount in the range of about 0.5% to about 1.5% by weight;

a pH adjuster in an effective amount in the range of about 0.001% to about 3% by weight.

7. The composition of claim 6, wherein the composition includes at least one silicone in an effective amount in the range of about 0.1% to about 10% by weight.

8. The composition of claim 6, wherein the composition includes at least one vitamin, chelating agent, protein, or an anti-oxidant.

9. The composition of claim 6, wherein the at least one pH adjuster comprises lactic acid or arginine.

* * * * *